(12) United States Patent
Kaschke et al.

(10) Patent No.: US 11,344,405 B2
(45) Date of Patent: May 31, 2022

(54) ARTIFICIAL EYE LENS HAVING MEDICINE REPOSITORY FORMED THEREIN, AND METHOD FOR PRODUCING AN ARTIFICIAL EYE LENS

(71) Applicant: Carl Zeiss Meditec AG, Jena (DE)

(72) Inventors: Michael Kaschke, Oberkochen (DE); Manfred Dick, Gefell (DE); Mario Gerlach, Glienicke-Nordbahn (DE)

(73) Assignee: Carl Zeiss Meditec AG, Jena (DE)

( * ) Notice: Subject to any disclaimer, the term of this patent is extended or adjusted under 35 U.S.C. 154(b) by 136 days.

(21) Appl. No.: 16/616,881

(22) PCT Filed: May 17, 2018

(86) PCT No.: PCT/EP2018/062921
§ 371 (c)(1),
(2) Date: Nov. 25, 2019

(87) PCT Pub. No.: WO2018/219670
PCT Pub. Date: Dec. 6, 2018

(65) Prior Publication Data
US 2021/0161655 A1 Jun. 3, 2021

(30) Foreign Application Priority Data
Jun. 1, 2017 (DE) ...................... 10 2017 112 085.8

(51) Int. Cl.
*A61F 2/16* (2006.01)
*B29D 11/02* (2006.01)

(52) U.S. Cl.
CPC .......... *A61F 2/1618* (2013.01); *A61F 2/1659* (2013.01); *B29D 11/023* (2013.01);
(Continued)

(58) Field of Classification Search
CPC .... A61F 2/1618; A61F 2/1601; A61F 2/1659; A61F 2002/1683; A61F 2002/169;
(Continued)

(56) References Cited

U.S. PATENT DOCUMENTS 4,781,718 A    11/1988   Lindstrom
4,889,421 A    12/1989   Cohen
(Continued)

FOREIGN PATENT DOCUMENTS

CN    1053301    7/1991
CN    1287899    12/2006
(Continued)

OTHER PUBLICATIONS

PCT/EP2018/062924, International Preliminary Report on Patentability dated Dec. 12, 2019. 16 Pages.
(Continued)

*Primary Examiner* — Paul B Prebilic
(74) *Attorney, Agent, or Firm* — Alston & Bird LLP (57) ABSTRACT

The invention relates to an artificial eye lens comprising an optical part, which has a first optical side as viewed in a direction of an optical principal axis of the artificial eye lens and an opposite second optical side, wherein a structure with at least one depression is formed in a haptic arrangement of the artificial eye lens and/or in a surround that surrounds the optical part at least in certain areas and that differs from the haptic arrangement, wherein the structure is formed as a micro-perforation with a multiplicity of perforation zones and at least some perforation zones are filled at least in certain areas with at least one medicament for the purposes of producing a medicament repository. The invention also relates to a method for producing such an artificial eye lens.

22 Claims, 2 Drawing Sheets

(52) U.S. Cl.
CPC . *A61F 2002/1683* (2013.01); *A61F 2240/001* (2013.01); *A61F 2250/0068* (2013.01)

(58) Field of Classification Search
CPC ........ A61F 2002/1696; A61F 2240/001; A61F 2250/0068; A61F 2250/0053; A61F 2250/0023; A61F 2250/0026; A61F 2250/005; A61F 2250/0085; A61F 2250/0091; A61F 2250/0097
See application file for complete search history.

(56) References Cited

U.S. PATENT DOCUMENTS

| | | |
|---|---|---|
| 4,976,732 A | 12/1990 | Vorosmarthy |
| 5,100,226 A | 3/1992 | Freeman |
| 5,142,411 A | 8/1992 | Fiala |
| 5,895,422 A | 4/1999 | Hauber |
| 2004/0032566 A1 | 2/2004 | Nakada et al. |
| 2006/0235514 A1 | 10/2006 | Silvestrini |
| 2006/0246112 A1 | 11/2006 | Snyder et al. |
| 2009/0198326 A1 | 8/2009 | Zhou et al. |
| 2009/0234448 A1 | 9/2009 | Weeber et al. |
| 2009/0287306 A1 | 11/2009 | Smith et al. |
| 2010/0082017 A1 | 4/2010 | Zickler et al. |
| 2010/0094414 A1 | 4/2010 | Downer et al. |
| 2010/0215720 A1* | 8/2010 | Garagorri Ganchegui ............... A61F 2/148 424/427 |
| 2011/0292335 A1 | 12/2011 | Schwiegerling |
| 2013/0268071 A1 | 10/2013 | Vilupuru et al. |
| 2014/0135920 A1* | 5/2014 | Sahler ............... A61F 2/1613 623/6.27 |
| 2014/0259657 A1 | 9/2014 | Riall et al. |
| 2015/0073549 A1 | 3/2015 | Webb et al. |
| 2015/0342725 A1 | 12/2015 | Cuevas et al. |
| 2015/0378065 A1* | 12/2015 | Knox ................. A61L 27/52 359/652 |
| 2016/0135947 A1 | 5/2016 | Webb et al. |
| 2016/0220352 A1 | 8/2016 | Choi et al. |
| 2016/0331519 A1 | 11/2016 | Kahook et al. |
| 2017/0042665 A1 | 2/2017 | Currie et al. |
| 2017/0119521 A1 | 5/2017 | Kahook et al. |
| 2017/0143477 A1 | 5/2017 | Christie et al. |
| 2018/0228601 A1* | 8/2018 | Hyun ............... A61F 2/1627 |

FOREIGN PATENT DOCUMENTS

| | | |
|---|---|---|
| CN | 1514423 | 6/2008 |
| CN | 202472154 U | 10/2012 |
| CN | 203220483 U | 10/2013 |
| CN | 102655823 | 4/2016 |
| DE | 3740533 A1 | 6/1989 |
| EP | 0589809 | 3/1994 |
| EP | 1250609 A2 | 10/2002 |
| WO | 9427169 A1 | 11/1994 |
| WO | WO9427169 | 11/1994 |
| WO | WO9525288 | 9/1995 |
| WO | WO03107076 | 12/2003 |
| WO | 2012138426 A2 | 10/2012 |

OTHER PUBLICATIONS

PCT/EP2018/062920, International Preliminary Report on Patentability dated Dec. 12, 2019. 16 Pages.
PCT/EP2018/062921, International Preliminary Report on Patentability dated Dec. 12, 2019. 18 Pages.
PCT/EP2018/062920, International Search Report dated Dec. 6, 2018.
PCT/EP2018/062921, International Search Report dated Dec. 6, 2018.
PCT/EP2018/062924, International Search Report dated Aug. 13, 2018. 14 pages.
Pin Yang et al: Femtosecond laser-pulse-induced birefringence in optically isotropic glass. Journal of Applied Physics 95, 5280 (2004); doi: 10.1063/1.1707231. 5 pages.
CN 201880035881.7, First Office Action dated Jun. 2, 2021. 20 pages.
CN 201880035713.8, First Office Action dated May 27, 2021. 17 pages.
U.S. Office Action of U.S. Appl. No. 16/616,878 dated Jul. 20, 2021; 10 pages.
U.S. Office Action of U.S. Appl. No. 16/616,881 dated Jul. 19, 2021; 15 pages.
U.S. Office Action of U.S. Appl. No. 16/616,028 dated Jul. 11, 2021; 12 pages.
CN 201880035896.3, First Office Action dated May 7, 2021. 16 pages.

* cited by examiner

ARTIFICIAL EYE LENS HAVING MEDICINE REPOSITORY FORMED THEREIN, AND METHOD FOR PRODUCING AN ARTIFICIAL EYE LENS

CROSS-REFERENCE TO RELATED APPLICATIONS

This application is a U.S. National Phase entry of International Application No. PCT/EP2018/062921, titled "Artificial eye lens having medicine repository formed therein, and method for producing an artificial eye lens," filed May 17, 2018, which claims priority to German Patent Application No. 10 2017 112 085.8, titled "Artificial eye lens having medicine repository formed therein, and method for producing an artificial eye lens", filed on Jun. 1, 2017, the contents of which are incorporated in this disclosure by reference in their entirety.

TECHNICAL FIELD

The invention relates to an artificial eye lens comprising an optical part, which has a first optical side as viewed in the direction of an optical principal axis of the eye lens and an opposite second optical side. The multifocal, artificial eye lens moreover comprises a haptic arrangement, by means of which the eye lens is positionable in an eye. The eye lens can have, in addition or as an alternative thereto, a surround that at least partially surrounds the optical part and differs from the haptic arrangement. A structure with at least one depression is formed in the haptic arrangement and/or in this surround. The invention furthermore also relates to a method for producing a lens of this type using a laser.

PRIOR ART

A variety of multifocal, artificial eye lenses are known from the prior art. In particular, to this end, intraocular lenses that replace the natural lens in the eye and are implanted in this respect are known.

US 2010/0082017 A1 discloses an intraocular lens in which slits are made in a haptic part and also in an optical part to modify the mechanical characteristic and also the structure characteristic of the lens. Said elongate slits are formed in the interior of the intraocular lens, in particular using a laser.

Moreover, US 2004/0032566 A1 discloses a method for marking an intraocular lens using a laser. The laser is used to perform a micro-perforation of the optical part of the lens.

It is also known that complications may occur when implanting artificial eye lenses, said complications possibly occurring during the operation, during the healing process following the operation or possibly even later still. Then, this may additionally require a post-treatment with a surgical intervention in turn in order to be able to heal the impairments.

PRESENTATION OF THE INVENTION

It is an object of the invention to develop an artificial eye lens whose functionality is improved. Moreover, it is an object of the invention to develop a method in order to be able to produce such a lens.

One aspect of the invention relates to an artificial eye lens having an optical part by way of which the optical imaging property of the eye lens is characterized. This optical part has a first optical side and a second optical side located opposite the former as viewed in the direction of the optical principal axis of said eye lens. The artificial eye lens furthermore has a haptic arrangement. The haptic arrangement is used to keep the eye lens in its position in an eye. The artificial eye lens has, in addition or as an alternative to the haptic arrangement, a surround that surrounds the optical part at least in certain areas and differs from the haptic arrangement. This surround is then neither a constituent part of the optical part nor is it a constituent part of arms of a haptic arrangement in particular, should such a haptic arrangement be present. The artificial eye lens comprises a structure that has at least one depression. The structure is formed as a micro-perforation with a multiplicity of individual and separate perforation zones. A micro-perforation should be understood to mean a perforation that has perforations with a longitudinal extent in the micrometer range and/or in the nanometer range. At least some perforation zones are formed as medicament repositories and are filled at least in certain areas with at least one medicament.

Such a configuration develops an artificial eye lens that contains at least one medicament within itself. This increases the functionality of the eye lens. In addition to its primary object of improving the optical visual acuity of an eye, this embodiment of the invention also still has inherent therein the additional function of serving as a medicament carrier. Consequently, what is also achieved by such an artificial eye lens is that the medicament is already present in the eye, respectively for a treatment by medicaments during a surgical intervention, in particular for implanting an artificial eye lens embodied as an intraocular lens, and/or for a duration of the healing process following such a surgical intervention and/or for ongoing maintenance of the healthy state even subsequent to the healing process. The medicament can also be administered individually in that case by virtue of emerging from a perforation zone. This can be caused by an interaction, for example with one or more media in the eye, in particular in the capsular bag, without an influence from the outside. In general, this administration of a medicament from a perforation zone can be implemented depending on the ambient conditions in the eye. In this context, a closure of a perforation zone produced, in particular, after filling said perforation zone with at least one medicament can also be removed, for example by dissolving. By way of example, this removal in the implanted state in an eye can be set in defined fashion, even in respect of the time and/or the time duration, already during the production of the artificial eye lens, depending on the thickness of the closure and/or the material. This also means that the time of the medicament administration and/or the time duration of the medicament administration from a perforation zone in the implanted state of the artificial eye lens can be set in individual fashion. Therefore, additional surgical interventions for promoting a healing process or for maintaining the healed state in an ongoing fashion, in particular after implanting such an eye lens into the eye, are no longer required or only required to a limited extent or in exceptional cases. Therefore, the impairment of a patient by subsequent interventions can be significantly reduced.

In particular, such a structure, and hence also a perforation zone, is embodied as a laser structure. This means that it is produced by a laser. As a result, the perforation zone can be produced with exceptional positional accuracy and/or exceptional geometric accuracy. This prevents unwanted dimensional tolerances and/or unwanted impairments of specific regions of the artificial eye lens, in particular of the optical part.

As a result of forming the micro-perforation in a region of the artificial eye lens that differs from the optical part, the optical part as such is not impaired either. Therefore, the optical imaging property remains unimpaired.

Having at least one such medicament repository then also allows the temporal administration of the at least one medicament from the medicament repository to be able to be implemented on an individual basis such that, depending on the situation for the respective healing process, an adequate, possibly very large amount of a medicament can also be administered very quickly in targeted fashion from a medicament repository in the implanted state of the eye lens. Likewise, this administration of the medicament from a medicament respiratory may possibly be implemented over a relatively long period of time, and also continuously, following the implantation of the eye lens into the eye.

In an advantageous embodiment, provision can be made for a first medicament to be introduced in at least one first perforation zone, which then represents a medicament repository, and a second medicament, differing from the first, to be introduced into at least one second perforation zone, differing from the first, said second perforation zone then also representing a dedicated medicament repository in turn. Provision can also be made for at least two different medicaments to be introduced in a common medicament repository. Likewise, more than two different medicaments may be introduced in a perforation zone as a medicament repository or at least three medicaments may be each housed in different dedicated separate perforation zones. Likewise, only a specific medicament may be introduced in one perforation zone and at least two mutually different medicaments may be introduced in at least one further perforation zone that differs from said one perforation zone. Depending on which medicament treatment, possibly preferred for the individual patient, is necessary or may be necessary and/or preferably depending on the period of time over which such a medicament treatment is necessary or may be necessary, it is then also possible to undertake an individual medicament-artificial design of these medicament repositories, even prior to the surgical intervention for introducing the eye lens into the eye. As a result of this, it is possible in this context to go into, for example, different earlier disorders of an eye and/or of a patient, for example should a patient be ill to a greater or lesser extent with diabetes and/or high blood pressure, etc. Consequently, a very patient-individual design of such an artificial eye lens can also be facilitated and the design of these medicament repositories can then be implemented very individually and adequately, depending on the patient's health condition.

Preferably, provision is made for the perforation zones that are filled at least in certain areas with at least one medicament to be formed as blind holes. Firstly, this allows a very individual and precise volume target to be produced, in particular by way of a laser, such that the amount of medicament introduced in such a perforation zone can also be set very accurately. Moreover, such a configuration prevents the unwanted emergence of a medicament in a direction not provided to this. In this form, the release or emergence of the medicament from the perforation zone then can be implemented only in the direction in which the blind hole has its blind hole opening.

Preferably, the blind holes have a funnel-shaped cross section such that the cross-sectional area of a blind hole reduces with increasing depth. Thus, there is less capillary action at the upper edge of the blind hole than at the base of the blind hole. This is advantageous since an administration of a medicament from the blind hole at different speeds is therefore achievable as a function of the aperture angle of the funnel-shaped blind hole.

Provision can be made for the micro-perforations, and hence the perforation zones, to be aligned in terms of their orientation or for at least two different perforation zones to have different orientations, also with their longitudinal axes of the perforation zones. Also as a result thereof, depending on which medicaments and/or the positions at which said medicaments should develop their effect, in particular predominantly develop their effect, it is possible to develop a structure that is individually designed in this respect. What can also be achieved thereby is that already the structuring alone is optionally produced adapted to the respective individual requirement profile, in particular that said structuring alone is embodied adapted to the patient. This also means that the number and/or the position and/or the orientation of the perforation zones and/or the positioning thereof can be produced on an individual basis.

This can also then be implemented in such a way that the perforation zones are formed in locally specified fashion at the haptic arrangement and/or the surround, wherein this is implemented depending on which medicaments and/or what amount of medicaments are/is required for this individual configuration of the eye lens.

The artificial eye lens preferably has a multifocal embodiment, i.e., at least a bifocal embodiment. The artificial eye lens is preferably an intraocular lens.

Provision is preferably made for the optical part of the multifocal, artificial eye lens to have a diameter of greater than 6 mm. As a result, this optical part also extends over a large pupil of an eye and/or a pupil of an eye that is to be opened very wide. In particular, this diameter of the optical part is greater than 6.5 mm.

Provision can be made for the structure of the perforation zones to have at least one ring that surrounds the optical principal axis. Additionally or alternatively, provision can also be made for the structure of the perforation zones to have at least one line with perforation zones that is oriented perpendicular to the optical principal axis. In particular, provision is made for the structure to have a star shape that surrounds the optical principal axis, said star shape being formed by arranging the perforation zones accordingly. This can, in turn, take account of individual requirements in respect of the required locality of the perforation zones with the medicaments and/or the possibly locally focused advantageousness of a relatively large amount of a medicament and/or the locally focused advantageousness of at least two different medicaments.

Preferably, the artificial eye lens has a further structure, which is formed as an artificial aperture stop or labeling in the optical part. This further structure, which consequently represents a structure that differs from the first structure formed in the haptic arrangement and/or in the surround, is formed in this optical part at a radial distance of greater than or equal to 3 mm from the optical principal axis. In particular, this further structure is formed as a micro-perforation with further perforation zones in this optical part. Provision can be made for this further structure to be formed as a laser structure and consequently be produced with a laser. These further perforation zones of the further structure can be filled with a dye. As a result of such a configuration, a surgeon can then easily identify, in simple fashion, the characterization of the eye lens in respect of its optical parameter values, for example and/or in respect of its orientation in the eye, for example in the case of a toric multifocal, artificial eye lens. To this end, provision can also be made for these further perforation zones to have a diameter of a few micrometers and for said further perforation zones to be produced by an ultrashort pulse laser. As a result of such a configuration, they do not have an impairing embodiment in respect of the optical imaging properties of the optical part but nevertheless facilitate the writing of visually readable information within the optical part, as illustrated above. Thus, for example, the position of cylinder axes, the refractive parameters and a type designation can also be produced accordingly as readable information in the optical part. Then, reading can also be reliably implemented in the aftercare of patients, for example by means of a slit lamp. In particular, this also allows such writing to be provided outside of a photopic pupil diameter and/or a mesopic pupil diameter.

By way of example, the perforation zones may also be formed here as ring-section-shaped cavity channels or else as closed rings in the form of cavity channels and may have inner coloring in the form of an aperture stop as an artificial pupil by virtue of an absorbing, biocompatible dye being introduced. These absorbing cavity channels can be used or embodied to suppress stray light under extreme visual conditions, possibly in diffractive structures. Additionally or alternatively, a fluorescent dye may also be provided for writing, wherein an infrared dye, for example, may be provided in this case.

As an alternative or in addition to a dye, an aperture stop may also be produced by means of a different degree of polymerization of the material of the artificial eye lens as a result of the action of a laser beam, in particular by way of multiphoton polymerization.

In an advantageous embodiment, provision is made for this micro-perforation of the further structure to be formed in such a way that the aperture stop is automatically modifiable in terms of its opening width as a function of the incident light. Hence, an adjustable light transmissivity is also created within the artificial eye lens and an artificial pupil is also provided in this respect. As already presented above, this can be achieved in particular by specific dyes, which are then introduced into this micro-perforation.

Preferably, provision is made for the micro-perforation to have a multiplicity of perforation zones which are disposed differently in respect of their spacing from one another. In particular, a statistical distribution with respect to one another can be formed here. Additionally or alternatively, the multiplicity of perforation zones can also be disposed differently with respect to one another in terms of their position and, here too, a statistical distribution of this position, in particular, can be realized. Additionally or alternatively, provision can also be made for this multiplicity of perforation zones to have a different embodiment with respect to one another in terms of their dimensions. In particular, a zone diameter of the perforation zone and/or a zone depth of a perforation zone can be accordingly designed differently in this case as a dimension.

In particular, at least one micro-perforation has at least one perforation zone that is a ring channel, which is consequently in particular an inherently closed, completely circumferential ring channel. This is advantageous, in particular, for the configuration of an artificial pupil with, in particular, a light transmissivity that is modifiable in the radial direction as a function of light.

Preferably, provision is made for the micro-perforation to have at least one perforation zone which is filled at least in certain areas with at least one dye that is wavelength selective, or intensity-dependent, in respect of the absorption behaviour.

Provision can also be made for a dye composition that varies in respect of the absorption behaviour in a radial direction with respect to the optical principal axis to be introduced into at least one perforation zone of this further structure, the absorption behaviour of said dye composition, when considered inwardly, increasing in the radial direction with respect to the optical principal axis with increasing intensity of the incident light.

In a further embodiment, provision can be made for the optical part of the eye lens to have a further structure that, as a micro-perforation, is embodied at least circumferentially about the optical principal axis of the optical part. This further structure is formed in the optical part in a first radius interval of between 1.5 mm and 2.5 mm from the optical principal axis and/or in a second radius interval of between 3.0 mm and 4.0 mm from the optical principal axis. Provision can be made for individual information possibilities about the eye lens to be able to be communicated by way of these structure rings embodied at individual points in the radial direction and, secondly, additional functionality of the eye lens to be able to be provided, in particular the production of an artificial pupil.

Provision can be made for a diffractive element to be formed on at least one side of the optical part. At least one side may also have a spherical or aspherical embodiment. Likewise, at least one side may have a toric surface profile. Likewise, ring-shaped zones that may be realized as Fresnel zones can be embodied on at least one side of the optical part. Provision can also be made of a configuration of such ring-shaped zones to the effect of such a ring-shaped zone having a principal sub-zone and a phase sub-zone adjoining this. In such a configuration, a phase sub-zone is not oriented parallel to the optical principal axis but, in this respect, is disposed at an inclination thereto and has a dedicated refractive power that contributes to the overall refractive power of this ring-shaped zone. Such a phase sub-zone produces an optical path length difference between two principal sub-zones directly adjoining this phase sub-zone in the radial direction in each case. The aforementioned configurations of the at least one side of the optical part can also be formed on their own or in any combinations.

In order to introduce additional diffractive properties in addition to the refractive power of the eye lens as a consequence of its refractive power and shape, provision in an advantageous embodiment is also made for a regular and hence uniform arrangement of this microstructure, and hence of the perforation zones, and a regular diameter production of these perforation zones to be formed.

Provision can also be made for a possible occurrence of a secondary cataract as a possible complication following a cataract operation in the case of an implanted eye lens, said secondary cataract being caused by the proliferation of epithelial cells toward the posterior capsular bag membrane. So as to at least alleviate this, provision is preferably made for microstructures, which also include nanostructures, to be embodied as perforation zones for modifying the roughness and wettability of the eye lens outside of the optical part, said microstructures being embodied as laser structures, in particular. As a result, cell adhesion and proliferation can be influenced. Consequently, guiding structures that promote a directed cell growth and consequently are able to at least significantly suppress the negative effects in this respect are able to be created. Nanostructures, in particular, which can be produced by interference structuring bring about a change in the distribution of the focal adhesion points of the cell and influence, inter alia, complex mechanisms such as the cell proliferation. Moreover, applying tightly arranged bores and semi-perforation zones as blind holes outside of the optical part facilitate an adhesion of the posterior capsular bag membrane. An example of such a structure can be a honeycomb structure, in which the perforation zones embodied as micro-bores are arranged and formed.

The invention furthermore also relates to a method for producing a multifocal, artificial eye lens according to the aforementioned aspects, in which a structure is produced with a laser apparatus, and a pulsed laser beam having a pulse length of between 100 fs and 20 ps, a wavelength of between 200 nm and 1100 nm, a pulse repetition rate of between 1 kHz and 10 MHz, a focus diameter of less than 5 µm and a power density of greater than $10^6$ W/cm$^2$ is produced and acts on the material of the artificial eye lens. The pulse length is preferably 300 fs and the wavelength is preferably 1060 nm or 532 nm or 355 nm. By way of disruptive machining, it is possible for preferably a wavelength of 256 nm and preferably of 213 nm to be provided for in particular ablative machining.

A further independent aspect of the invention relates to an artificial eye lens having an optical part by way of which the optical imaging property of the artificial eye lens is characterized. This optical part has a first optical side and a second optical side located opposite the former as viewed in the direction of the optical principal axis of said artificial eye lens. The artificial eye lens has a structure that is embodied as a micro-perforation and that is formed as surrounding the optical principal axis of the optical part at least in certain areas. The optical part has a diameter of greater than 6 mm, in particular greater than or equal to 6.5 mm. The structure is formed as an artificial aperture stop in the optical part as a micro-perforation in the optical part at a radial distance of greater than or equal to 3 mm from the optical principal axis.

A further independent aspect of the invention relates to an artificial eye lens having an optical part by way of which the optical imaging property of the artificial eye lens is characterized. This optical part has a first optical side and a second optical side located opposite the former as viewed in the direction of the optical principal axis of said artificial eye lens. The multifocal, artificial eye lens furthermore has a haptic arrangement. The haptic arrangement is used to keep the eye lens in its position in the eye. The multifocal, artificial eye lens has, in addition or as an alternative to the haptic arrangement, a surround that surrounds the optical part at least in certain areas and differs from the haptic arrangement. This surround is then neither a constituent part of the optical part nor is it a constituent part of a haptic arrangement, should such a haptic arrangement be present. The multifocal, artificial eye lens comprises a structure that has at least one depression. The structure is formed as a micro-perforation with a multiplicity of individual and separate perforation zones. The perforation zones are formed as blind holes. The perforation zones form a network structure. In particular, the network structure has a honeycomb form.

A further independent aspect of the invention relates to an artificial eye lens having an optical part by way of which the optical imaging property of the artificial eye lens is characterized. This optical part has a first optical side and a second optical side located opposite the former as viewed in the direction of the optical principal axis of said artificial eye lens. The artificial eye lens has a structure that is embodied as a micro-perforation and that is formed as surrounding the optical principal axis of the optical part at least in certain areas. The structure is formed in the optical part. The structure is formed in the optical part in a first radius interval of between 1.5 mm and 2.5 mm from the optical principal axis and/or is formed in a second radius interval of between 3.0 mm and 4.0 mm from the optical principal axis.

Embodiments of the first independent aspect of the invention should be considered to be advantageous embodiments of the further independent aspects. A corresponding statement applies to the production method.

Further features of the invention are evident from the claims, the figures and the description of the figures. The features and feature combinations mentioned in the description above and the features and feature combinations mentioned in the description of the figures below and/or only shown in the figures may be used not only in the respectively specified combination, but also in other combinations, without departing from the scope of the invention. Hence, embodiments of the invention which are not explicitly shown and explained in the figures but which emerge from the explained embodiments by way of separate feature combinations and which are producible should also be considered to be comprised and disclosed. Embodiments and feature combinations which therefore do not have all the features of an originally phrased independent claim should also be considered to be disclosed. Furthermore, embodiments and feature combinations, in particular by virtue of the embodiments explained above, which go beyond or deviate from the feature combinations explained in the dependency references of the claims should be considered to be disclosed.

The concrete values indicated in the documents for parameters and indications concerning ratios of parameters or parameter values for the definition of exemplary embodiments of the eye lens should be considered to be concomitantly encompassed by the scope of the invention even in the context of deviations, for example on account of measurement errors, system faults, DIN tolerances, etc., which means that explanations relating to substantially corresponding values and indications should also be understood thereby.

BRIEF DESCRIPTION OF THE DRAWINGS

Exemplary embodiments of the invention are explained in greater detail below with reference to schematic drawings. In the figures.

PREFERRED EMBODIMENTS OF THE INVENTION

In the figures, identical or functionally equivalent elements are provided with the same reference signs.

Figure 1:
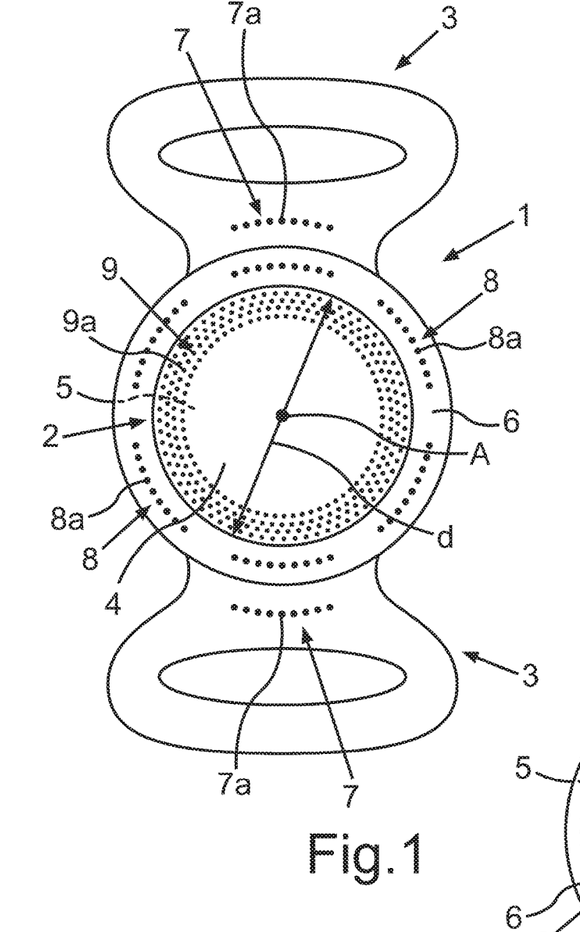
FIG. 1 shows a plan view of a first exemplary embodiment of an artificial eye lens according to the invention in a schematic illustration.

FIG. 1 shows a plan view of a first exemplary embodiment of a multifocal, artificial eye lens 1, which is in this case an intraocular lens. The artificial eye lens 1 comprises an optical part 2 and, adjacent thereto, a haptic arrangement 3. The artificial eye lens 1 is foldable and may be introduced into an eye through a small incision. The optical part 2, which is essential to the optical imaging property of the artificial eye lens 1, has an optical principal axis A, which is oriented perpendicular to the plane of the figure and, in particular, is perpendicular to a principal plane of the optical part 2. Moreover, when viewed in the direction of this optical principal axis A, the optical part 2 comprises a first optical area or optical side 4, which may be a front side, and comprises opposite thereto a second optical area or optical side 5, which may be a back side. In the implanted state of the eye lens 1 in the eye, the front side faces the cornea, whereas the back side faces away from this cornea.

In addition to the haptic arrangement 3, or as an alternative thereto, the artificial eye lens 1 may have a surround 6. The surround 6 is not a constituent part of the optical part 2 and consequently does not contribute to the optical imaging property of the artificial eye lens 1 and hence does not contribute to the optical imaging property of the optical part 2 either. The same applies to the haptic arrangement 3. The surround 6 is embodied here as a completely surrounding ring. However, the surround 6 may also be formed as a ring portion only, and for example only be formed in the region between a haptic arrangement 3 and the optical part 2, for example as a bridge or connector between these components.

Figure 2:
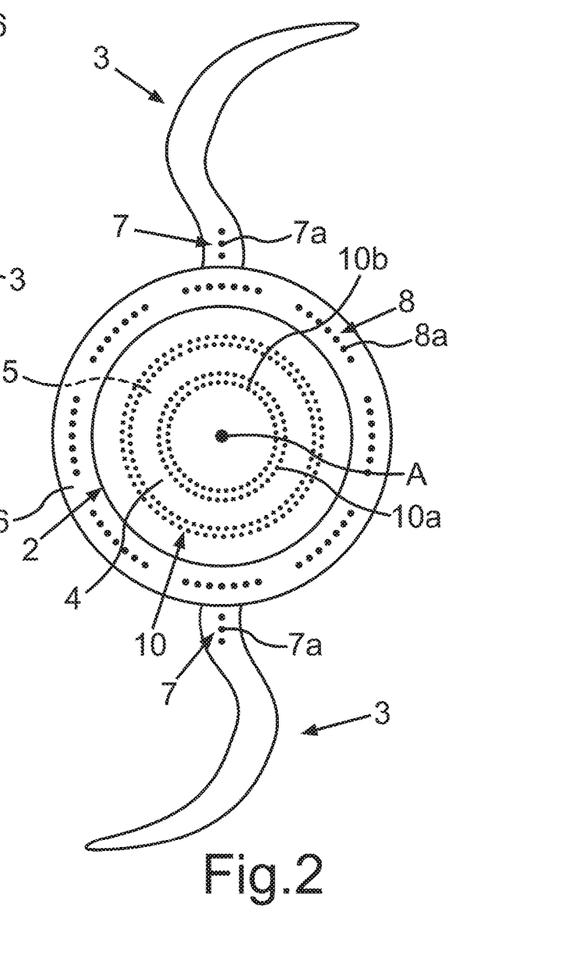
FIG. 2 shows a plan view of a second exemplary embodiment of an artificial eye lens according to the invention in a schematic illustration.

FIG. 2 shows a plan view of a further exemplary embodiment of a multifocal, artificial eye lens 1 embodied as an intraocular lens. Said lens differs from the embodiment in FIG. 1 by way of the different haptic arrangement 3. Here, the eye lens 1 is also held in the eye, particularly in the capsular bag, by means of the haptic arrangement 3.

Figure 3:
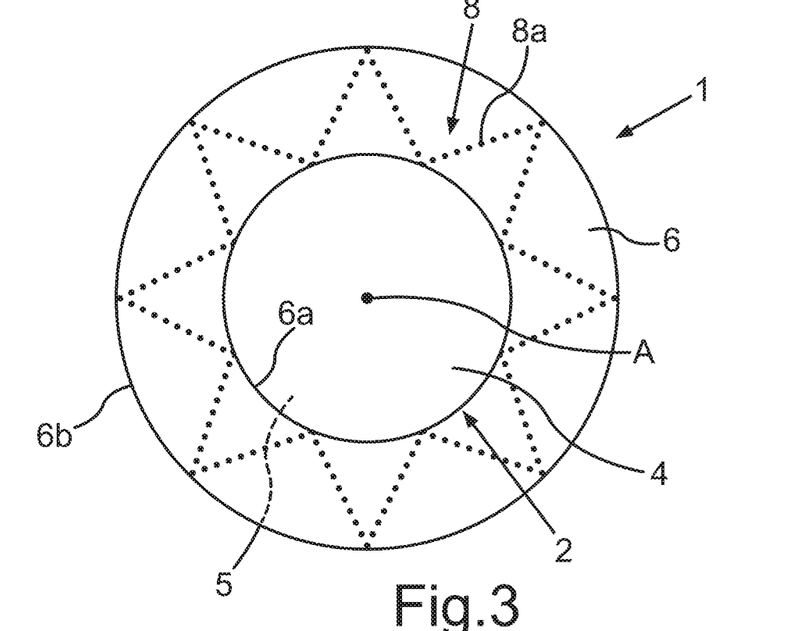
FIG. 3 shows a plan view of a third exemplary embodiment of an artificial eye lens according to the invention in a schematic illustration.

FIG. 3 shows a further exemplary embodiment of an eye lens 1 in a plan view. Here, the surround 6 is also preferably embodied as a surrounding ring. The haptic arrangement can also be dispensed with in this case and the functioning thereof can also be adopted by the surround 6. However, provision can also be made for ring portions of this ring to form an incompletely surrounding surround 6 around the optical part 2 and for other ring portions to form a haptic arrangement.

The optical sides 4 and 5 are curved in the embodiments, preferably in non-planar fashion, in particular convexly. In particular, a diffractive profile and/or a toric profile is formed on at least one optical side 4, 5 on this convex, particularly spherical or aspherical, base form.

In principle, it is also possible for differently shaped and configured haptic arrangements 3 and/or surrounds 6 to be provided.

The multifocal, artificial eye lens 1 as shown in FIG. 1 and FIG. 2 in different exemplary embodiments has a structure 7 of the haptic arrangement 3, should the latter be present, and/or has a structure 8 of the surround 6, should the latter be present. It should be revealed here that both the local positions and the geometric configurations of the structures 7 and 8 should only be understood symbolically and should be understood to elucidate these structures and that these do not represent a complete specification in this respect. The structure 7 is formed as a micro-perforation with a multiplicity of perforation zones 7a. In particular, the perforation zones 7a are embodied as blind holes and are embodied as micro-bores. To this end, they are configured as a laser structure and produced by a laser apparatus.

At least some of these perforation zones 7a are formed as medicament repositories and are consequently filled with at least one medicament in certain areas. Additionally or alternatively, provision can also be made for the structure 8 to be a micro-perforation and to have a multiplicity of perforation zones 8a. For reasons of clarity, FIG. 1 indicates such an illustration of perforation zones 8a at only one point. These perforation zones 8a, too, are preferably embodied as blind holes and produced by a laser apparatus. Here, too, at least some of the perforation zones 8a are formed as medicament repositories and are filled at least in certain areas with at least one medicament. The perforation zones 7a and/or 8a can be formed in one or more lines. From the geometric point of view, they can be formed to be the same or different from one another. They can have a regular arrangement or be disposed with a statistical distribution.

Provision can be made for the structure 8 to have at least one ring that surrounds the optical principal axis A. Additionally or alternatively, the structure 8 can have a structure region that is oriented in radial fashion with respect to the optical principal axis A. Other geometric configurations of perforation zones may also be formed in the structure 7 and/or the structure 8.

In one exemplary embodiment, the optical part 2 can have a diameter d that is greater than 6 mm, in particular greater than 6.5 mm, more particularly independently of the local and geometric configuration of a structure 7 and/or 8.

The optical part 2 can have a structure 9, in particular likewise produced by the laser apparatus as a laser structure, said structure being able to be a further structure 9 that is embodied as an artificial aperture stop. In particular, this artificial aperture stop is formed in the optical part 2 at a radial distance of greater than or equal to 3 mm from the optical principal axis A should this optical part 2 have a diameter of greater than 6 mm. This further structure 9, too, is embodied as a micro-perforation in particular. In particular, this further structure 9 is filled with at least one dye. Preferably, this micro-perforation of the further structure 9 is formed in such a way that the aperture stop is automatically modifiable in terms of its opening width as a function of the incident light. As a result, an artificial pupil is formed in the artificial eye lens 1 itself.

This micro-perforation of the further structure 9 has, in particular, a multiplicity of perforation zones 9a, which are disposed differently with respect to one another in terms of their spacing, which more particularly are disposed with a statistical distribution with respect to one another, and/or which are disposed differently with respect to one another in terms of their position, which more particularly are disposed with a statistical distribution with respect to one another, and/or which have a different embodiment with respect to one another in terms of their dimensions, in particular a perforation zone diameter and/or a perforation zone depth.

Provision can also be made for this further structure 9 to have at least one ring that completely surrounds the optical principal axis A, more particularly to have two such rings that completely surround the optical principal axis, said rings having an embodiment spaced apart from one another in the radial direction with respect to the optical principal axis A. Provision can be made for this further structure 9, in particular, to respectively have a ring made of micro-perforations and hence perforation zones, which are embodied as micro-bores, in a first radius interval of between 1.5 mm and 2.5 mm from the optical principal axis A and/or in a second radius interval of between 3.0 mm and 4.0 mm from the optical principal axis. However, this configuration can be embodied by a structure that once again is a further structure too, and in turn different from, the further structure 9 in this regard.

The various exemplary embodiments explained in relation to FIG. 1 are also possible for the configuration according to FIG. 2 and FIG. 3. FIG. 2 schematically shows the once again further structure 10 with the perforation rings presented at the specific radius intervals, which is explained in FIG. 1 but not plotted there for reasons of clarity. These rings 10a and 10b at the radius intervals between 1.5 mm and 2.5 mm and between 3.0 mm and 4.0 mm are likewise only illustrated symbolically here for reasons of clarity.

FIG. 3 shows a specific geometry of the structure 8, which represents a star shape in this case. This star shape extends from an inner edge 6a of the surround 6 to an outer edge 6b of this surround 6. The perforation zones 8a are likewise shown symbolically here. Such a star shape of the structure 8 can also be provided in the exemplary embodiments in FIG. 1 and FIG. 2. In order to elucidate this star shape, the surround is illustrated in a radially enlarged fashion in comparison with the optical part 2.

In the embodiments, provision can be made for some of the perforation zones 7a and/or 8a to have an open embodiment in the direction of the optical side 4 of the optical part 2 or for the perforation zones 7a and 8a to have an open embodiment only in the direction of the optical side 5 of the optical part 2. Provision can also be made for some of the perforation zones 7a and/or 8a to have an open embodiment in the direction of the optical side 4 and for some of the perforation zones 7a and 8a to have an open embodiment in the direction of the optical side 5. These alternatives are particularly suitable when these perforation zones 7a and 8a are embodied as blind holes. A form of the perforation zones and their openings that, in turn, are individual in this respect is facilitated here, and so a specific administration of the medicament and/or of the medicaments is facilitated in an individually local fashion in this case, too.

Figure 4:
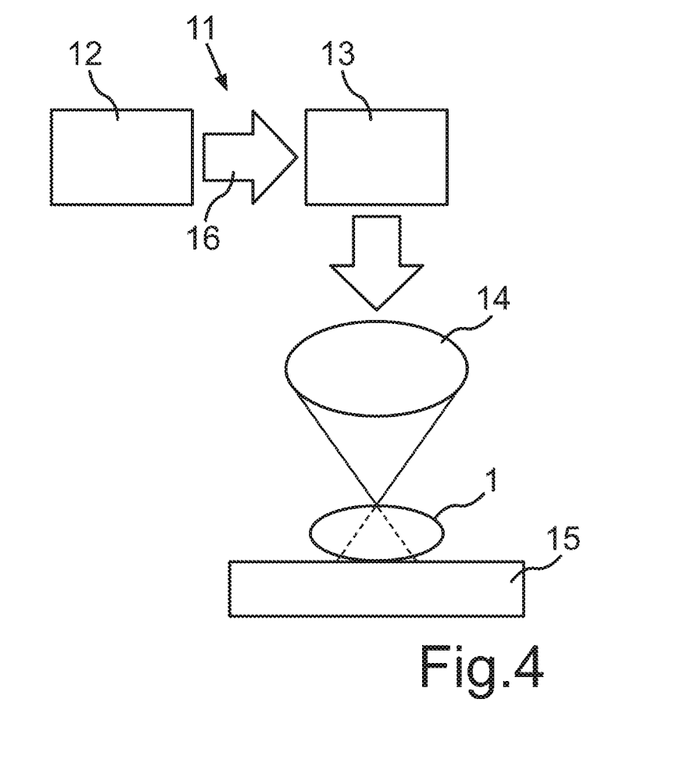
FIG. 4 shows a simplified schematic illustration of a laser apparatus for producing structuring on an eye lens according to FIG. 1 to 3.

FIG. 4 shows a schematic illustration of a laser apparatus 11, which is configured for producing a multifocal, artificial eye lens 1. In particular, this laser apparatus 11 facilitates the production of a structure 7 and/or a structure 8 and/or a structure 9 and/or a structure 10. The laser apparatus 11 has at least one laser 12, which is an ultrashort pulse laser. Said laser apparatus 11 has an in particular three-dimensionally settable scanner 13, with which the pulsed laser beam of the laser 12 is adjustable. The laser apparatus 11 furthermore has a focusing optical unit 14 arranged downstream of the scanner 13 in the beam path. The laser apparatus 11 furthermore has a receptacle 15 on which the artificial eye lens 1 is placed so as to be able subsequently to allow the desired structuring to form with the laser beam 16 focused by way of the focusing optical unit 14. The laser beam 16 with its laser pulses is produced in particular with a pulse length of between 100 fs and 20 ps, in particular a wavelength of between 200 nm and 1100 nm, in particular a pulse repetition rate of between 1 kHz and 10 MHz, in particular a focus diameter of less than 5 μm, and in particular a power density of greater than $10^8$ W/cm$^2$. In particular, multiphoton absorption is made possible here. The focusing optical unit 14 can have a numerical aperture of greater than 0.1, preferably greater than 0.3, and in particular greater than 0.5. The production of focus diameters of less than 5 μm, in particular of less than 2 μm, is also possible with the laser apparatus 11. In this case, a power density of the focused laser beam of greater than $10^{10}$ W/cm$^2$ is sensible to achieve an optical disruption (photodisruption) of the polymer material of the artificial eye lens when for example no linear absorption of the polymer material supports this effect. In order to achieve only a non-linear interaction in the polymer material of the artificial eye lens 1, a power density of less than $10^{10}$ W/cm$^2$ is also provided, which does not result in photodisruption, but can change optical and/or mechanical or else associated hygroscopic material properties. In order to ensure a high machining efficiency of the artificial eye lens, a repetition rate of the ultrashort laser pulses of the laser beam 16 in the range of 1 kHz to 10 MHz is advantageous. Pulse energies in the sub-μJ range are used here. In particular, at a repetition rate of greater than 1 MHz, a pulse energy of less than 1 μJ is also provided owing to cumulative interaction effects.

In addition to the explanation relating to the configurations as medicament repositories at least in certain areas, the structure 7 and/or the structure 8, in particular, can also be embodied, in particular, in micro-sleeves or nano-sleeves and, in particular, in the form of rings surrounding the optical principal axis A at least in certain areas. As a result, a change in the roughness and wettability of the artificial eye lens 1 is possible in these regions. This is advantageous since the occurrence of secondary cataract can consequently be reduced or targeted control thereof is facilitated.

Additionally, in the case of the structure 8, in particular, individual perforation zones can be provided and formed in the edge region in order to facilitate improved adhesion with the capsular bag. As a result, the positional arrangement of the eye lens 1 in the capsular bag is likewise improved. The arrangement can be formed not only here as a honeycomb structure, for example, and so the perforation zones 8a provided to this end are formed accordingly with respect to one another. These configurations can be realized in addition to the configurations already explained above and/or optionally with respect thereto.

The invention claimed is:

1. An artificial eye lens comprising:
   an optical part that has a first optical side as viewed in a direction of an optical principal axis of the artificial eye lens and an opposite second optical side; and
   a non-optical part comprising at least one of (a) a haptic arrangement or (b) a surround that surrounds the optical part at least in certain areas,
   wherein a first structure with at least one depression is formed in at least a portion of the non-optical part of the artificial eye lens,
   wherein the first structure is formed as a micro-perforation with a multiplicity of perforation zones and at least some perforation zones are filled at least in certain areas with at least one medicament creating at least one medicament repository,
   wherein a second structure is formed in the optical part of the artificial eye lens, and
   wherein the second structure is formed as an artificial aperture stop in the optical part as a micro-perforation in the optical part at a radial distance of greater than or equal to 3 mm from the optical axis.

2. The artificial eye lens of claim 1, wherein the perforation zones that are filled at least in certain areas with at least one medicament are formed as blind holes.

3. The artificial eye lens of claim 1, wherein the optical part has a diameter of greater than 6 mm.

4. The artificial eye lens of claim 1, wherein the optical part has a diameter greater than 6.5 mm.

5. The artificial eye lens of claim 2, wherein the optical part has a diameter of greater than 6 mm.

6. The artificial eye lens of claim 2, wherein the optical part has a diameter greater than 5 mm.

7. The artificial eye lens of claim 1, wherein the micro-perforation of the second structure is formed in such a way that the micro-perforation is configured to automatically modify an opening width of the aperture stop as a function of incident light.

8. The artificial eye lens of claim 1, wherein the micro-perforation of the first structure has a multiplicity of perforation zones that are disposed differently with respect to one another in terms of their spacing.

9. The artificial eye lens of claim 8, wherein the perforation zones are disposed differently with respect to one another in terms of their position.

10. The artificial eye lens of claim 8, wherein the perforation zones have different embodiment with respect to one another in terms of their dimensions.

11. The artificial eye lens of claim 1, wherein the micro-perforation has at least one perforation zone which is a ring channel.

12. The artificial eye lens as claimed in claim 1, wherein the micro-perforation has at least one perforation zone which is filled at least in certain areas with at least one dye that is wavelength selective with respect to the absorption behaviour.

13. The artificial eye lens of claim 11, wherein a dye composition that varies with respect to the absorption behaviour in a radial direction with respect to the optical principal axis is introduced into at least one perforation zone, the absorption behaviour of said dye composition increases in the radial direction with respect to the optical principal axis with increasing intensity of incident light.

14. The artificial eye lens of claim 1, wherein the optical part comprises a second structure which is formed as a micro-perforation and as surrounding the optical principal axis of the optical part at least in certain areas, wherein the second structure is formed in the optical part in a first radius interval of between 1.5 mm and 2.5 mm from the optical principal axis.

15. The artificial eye lens of claim 14, wherein the second structure has a second radius interval of between 3.0 mm and 4.0 mm from the optical principal axis.

16. The artificial eye lens of claim 1, wherein the optical part comprises a second structure which is formed as a micro-perforation and as surrounding the optical principal axis of the optical part at least in certain areas, wherein the second structure is formed in the optical part in a radius interval of between 3.0 mm and 4.0 mm from the optical principal axis.

17. The artificial eye lens of claim 1, wherein the first structure is formed by a laser.

18. The artificial eye lens of claim 1, wherein the first structure and the second structure are each formed by a laser.

19. A method for producing an artificial eye lens, the method comprising:
causing a first structure to be produced in a haptic arrangement of the artificial eye lens with a laser apparatus; and
causing a second structure to be produced in an optical part of the artificial eye lens with the laser apparatus, wherein the optical part has a first optical side as viewed in a direction of an optical principal axis of the artificial eye lens and an opposite second optical side, and
wherein the first structure formed in the haptic arrangement comprises at least one depression is formed in the haptic arrangement,
wherein the first structure is formed as a micro-perforation with a multiplicity of perforation zones and at least some perforation zones are configured to be filled at least in certain areas with at least one medicament creating at least one medicament repository, and
wherein the second structure is formed as an artificial aperture stop in the optical part as a micro-perforation in the optical part at a radial distance of greater than or equal to 3 mm from the optical axis.

20. The method of claim 19, wherein at least one of (a) causing the first structure to be produced in the haptic arrangement or (b) causing the second structure to be produced in the optical part comprises causing the laser apparatus to generate a pulsed laser beam having a pulse length of between 100 fs and 20 ps, a wavelength of between 200 nm and 1100 nm, a pulse repetition rate of between 1 kHz and 10 MHz, a focus diameter of less than 5 and a power density of greater than $10^8$ W/cm$^2$.

21. An artificial eye lens comprising:
an optical part that has a first optical side as viewed in a direction of an optical principal axis of the artificial eye lens and an opposite second optical side;
a surround that surrounds the optical part at least in certain areas;
a haptic arrangement that differs from the surround; and
a first structure formed at least in part in the haptic arrangement of the artificial eye lens and at least in part in the surround of the artificial eye lens,
wherein the first structure comprises at least one depression,
wherein the first structure is formed as a micro-perforation with a multiplicity of perforation zones and at least some perforation zones are filled at least in certain areas with at least one medicament creating at least one medicament repository.

22. An artificial eye lens comprising:
an optical part that has a first optical side as viewed in a direction of an optical principal axis of the artificial eye lens and an opposite second optical side; and
at least one of (a) a surround that surrounds the optical part at least in certain areas or (b) a haptic arrangement that differs from the surround; and
a first structure formed in at least in portion of the at least one of (a) the surround or (b) the haptic arrangement,
wherein the first structure is formed as a micro-perforation with a multiplicity of perforation zones and at least some perforation zones are filled at least in certain areas with at least one medicament creating at least one medicament repository, and
wherein at least one of the perforation zones is formed as blind holes having a funnel-shaped cross-section such that respective cross-sectional areas of the blind holes reduce with increasing depth.

* * * * *

UNITED STATES PATENT AND TRADEMARK OFFICE
CERTIFICATE OF CORRECTION

| | |
|---|---|
| PATENT NO. | : 11,344,405 B2 |
| APPLICATION NO. | : 16/616881 |
| DATED | : May 31, 2022 |
| INVENTOR(S) | : Michael Kaschke et al. |

It is certified that error appears in the above-identified patent and that said Letters Patent is hereby corrected as shown below:

In the Claims

In Column 14, Line 20, Claim 20, delete "5" and insert -- 5 µm, --, therefor.

Signed and Sealed this
Twenty-ninth Day of November, 2022

*Katherine Kelly Vidal*

Katherine Kelly Vidal
*Director of the United States Patent and Trademark Office*